United States Patent [19]

Hsia

[11] Patent Number: 5,287,380
[45] Date of Patent: Feb. 15, 1994

[54] METHOD AND APPARATUS FOR GENERATING LONG OUTPUT PULSES FROM FLASHLAMP-EXCITED LASERS

[75] Inventor: James C. Hsia, Andover, Mass.

[73] Assignee: Candela Laser Corporation, Wayland, Mass.

[21] Appl. No.: 20,118

[22] Filed: Feb. 19, 1993

[51] Int. Cl.$^5$ .............................................. H01S 3/09
[52] U.S. Cl. ........................................ 372/69; 372/70
[58] Field of Search ................... 372/38, 53, 69, 70; 606/2

[56] References Cited

U.S. PATENT DOCUMENTS

| | | | |
|---|---|---|---|
| 3,178,657 | 4/1965 | Morse | 372/70 |
| 3,760,295 | 9/1973 | Lankard et al. | 331/94.5 |
| 3,829,791 | 8/1974 | Schwartz | 331/94.5 |
| 3,863,105 | 1/1975 | Ewanizky | 315/245 |
| 3,914,709 | 10/1975 | Pike et al. | 331/94.5 |
| 4,398,129 | 8/1983 | Logan | 315/208 |
| 4,525,842 | 6/1985 | Myers | 372/92 |
| 4,627,063 | 12/1986 | Hosokawa | 372/70 |
| 4,829,262 | 5/1989 | Furumoto | 330/4.3 |
| 4,860,302 | 8/1989 | James | 372/70 |
| 4,917,084 | 4/1990 | Sinofsky | 606/7 |
| 4,981,138 | 1/1991 | Deckelbaum et al. | 128/665 |
| 5,041,108 | 8/1991 | Fox et al. | 606/7 |
| 5,066,293 | 11/1991 | Furumoto | 606/9 |
| 5,195,104 | 3/1993 | Geiger et al. | 372/70 |

Primary Examiner—Georgia Y. Epps
Assistant Examiner—Robert E. Wise
Attorney, Agent, or Firm—Testa, Hurwitz & Thibeault

[57] ABSTRACT

A flashlamp-excited laser for producing a pulsed beam of laser light of long duration (e.g., greater than 500 microseconds) comprises a flashlamp driven by a pulse forming circuit which generates a ramp pulse having an amplitude generally increasing with time during substantially the entire duration of the pulsed beam of laser light produced by the laser.

13 Claims, 3 Drawing Sheets

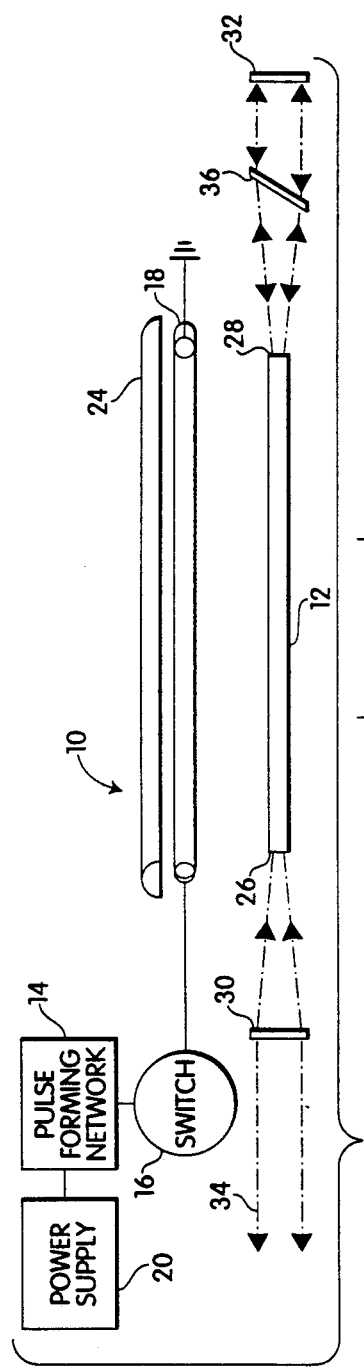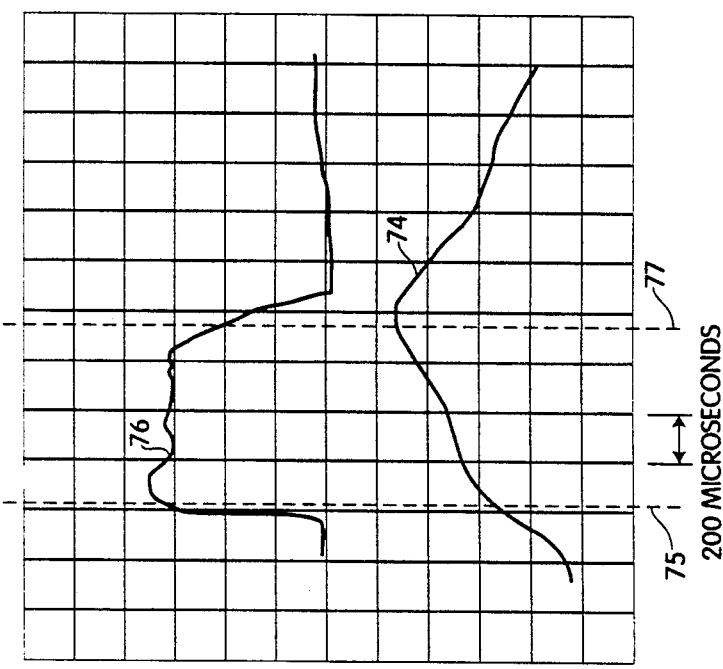
Fig. 1
Fig. 2B

200 MICROSECONDS

200 MICROSECONDS

METHOD AND APPARATUS FOR GENERATING LONG OUTPUT PULSES FROM FLASHLAMP-EXCITED LASERS

FIELD OF THE INVENTION

This invention relates to a method and apparatus for generating long output pulses from lasers, and more particularly, to a method and apparatus for achieving output light pulses of long duration from flashlamp-excited lasers.

BACKGROUND OF THE INVENTION

Some medical techniques utilizing lasers can be performed with better and more optimal results by employing a laser which generates output laser light pulses having a relatively long duration. One such medical technique is selective photothermolysis which is used, for example, to treat cutaneous vascular lesions. In selective photothermolysis, targeted tissues are heated by laser light (e.g., light generated by a flashlamp-excited liquid dye laser) having a wavelength selected to be specifically absorbed by the targeted tissue. In treating cutaneous vascular lesions, the benefits afforded by a flashlamp-excited liquid dye laser (FEDL) which generates output laser light pulses of long duration include improved clearing of the lesion, fewer treatment sessions, reduced incidence of hyper pigmentation, and a reduced transient purpura.

Conventional flashlamp-excited lasers including flashlamp-excited dye lasers and FEDLs typically produce output laser light pulses lasting between approximately 0.1 and 100 microseconds. Attempts to extend the duration of the output light pulse of a FEDL beyond this range typically result in thermal optical distortions of a liquid dye medium of the FEDL which cause the laser action (i.e., "lasing") of the FEDL to self-terminate. These thermal optical distortions of the liquid dye medium are induced, in general, by the excitation provided to the flashlamp.

SUMMARY OF THE INVENTION

In general, in one aspect, the invention features a method of generating a pulsed beam of laser light of long duration (e.g., greater than 500 microseconds) from a flashlamp-excited laser by first generating a ramp current pulse having an amplitude which generally increases with time during substantially the entire duration of the pulsed beam of laser light, and then driving the flashlamp-excited laser with the ramp pulse.

In another aspect, the invention features generally a flashlamp-excited laser for producing a pulsed beam of laser light of long duration, such as greater than 500 microseconds. The laser includes a flashlamp driven by a pulse forming circuit which generates a ramp pulse having an amplitude generally increasing with time during substantially the entire duration of the pulsed beam of laser light.

Embodiments of either aspect of the invention can include the following features. The amplitude of the ramp pulse preferably increases by a factor of about 2 or greater during substantially the entire duration of the pulsed beam of laser light. The pulsed beam of laser light preferably has an energy level of about 0.5 Joules or greater. A lasing medium associated with the flashlamp-excited laser can be a dye carried by a liquid. The flashlamp-excited laser can be used to treat cutaneous vascular lesions.

Other aspects, features, and advantages of the invention will become apparent from the following description and from the claims.

BRIEF DESCRIPTION OF THE DRAWINGS

FIG. 1 is a functional block diagram of a laser system featuring long output pulse duration according to the invention.

FIGS. 2A and 2B are each a graphical illustration of a ramped-amplitude excitation pulse according to the invention and a resulting long output pulse produced by the laser system of FIG. 1.

DETAILED DESCRIPTION

The invention generally relates to a method and apparatus for generating a pulsed beam of laser light of relatively long duration from a flashlamp-excited laser, such as a flashlamp-excited dye laser or a flashlamp-excited liquid dye laser (FEDL). In a FEDL, a lasing medium typically in the form of a dye carried by a liquid is directed through an elongated dye cell. The laser preferably is capable of producing pulsed beams of laser light having relatively high energy levels such as at least about 0.5 Joules. In general, the laser can be any flashlamp-excited laser whose lasing threshold increases with time. The long duration of the output laser light pulse is achieved by driving a flashlamp (or flashlamps) in the laser with a ramped input pulse whose amplitude generally increases with time during substantially the entire duration of the output laser light pulse. The amplitude of the ramped input pulse preferably at least doubles in value as measured at points corresponding to substantially the beginning and end of the output laser light pulse.

Figure 3:
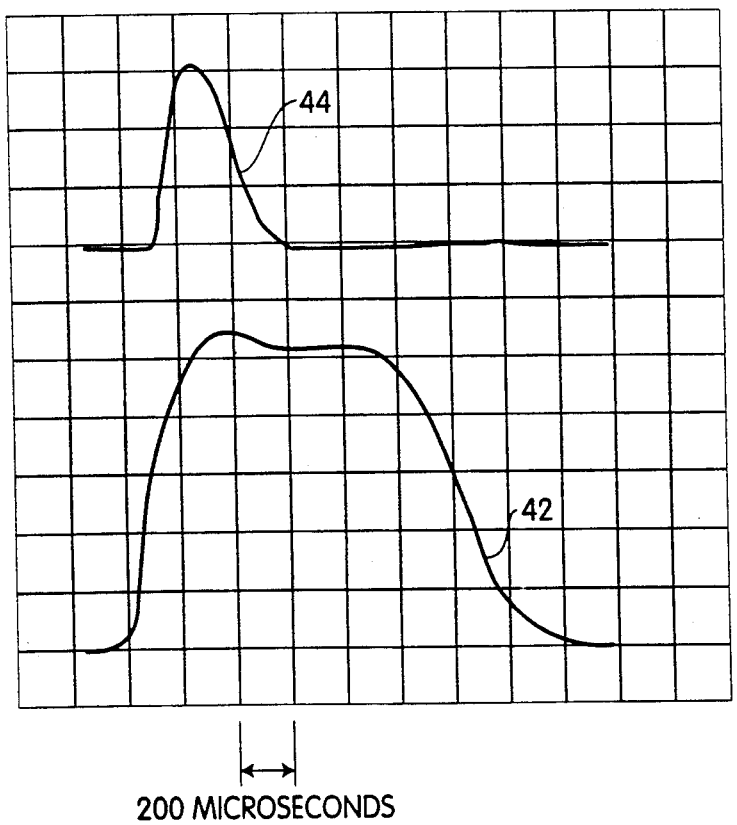
FIG. 3 is a graphical illustration of a typical excitation pulse applied to, and an output pulse produced by, a conventional laser system.

Referring to FIG. 3, in a conventional flashlamp-excited laser system, an input or excitation pulse 42 provided to a flashlamp typically is approximately constant and the duration of a resulting output laser pulse 44 typically is about 400 microseconds or less. As is typical in such conventional laser systems, the output pulse 44 initially increases but then rapidly decreases while the excitation pulse 42 is held relatively constant. Thus, as illustrated by FIG. 3, such conventional laser systems have a tendency to self-terminate or quench because the lasing threshold cannot be maintained for longer than about 400 microseconds when a relatively constant input pulse such as the excitation pulse 42 is applied.

Referring to FIG. 1, one embodiment of a laser system in accordance with the invention includes a flashlamp-excited laser 10. In this embodiment, a lasing medium in the form of a dye carried by a liquid is directed through an elongated dye cell 12 from one end to the other. The lasing medium typically is maintained at a uniform and constant temperature. In the disclosed embodiment, an excitation pulse forming network 14 generates a ramped output pulse and applies the ramped pulse, typically through a switching device 16, such as an ignitron or SCR, to a flashlamp 18 to excite the lasing medium. The ramped current pulse generated by the network 14 causes the flashlamp 18 to discharge (i.e., produce light) with an intensity that increases with time. This light of increasing intensity from the flashlamp 18 excites the lasing medium in the dye cell 12 and causes lasing action which results in a pulsed beam of laser light 34 having a duration greater than 500 microseconds, as described below. A power supply 20 typically is associated with the excitation pulse forming network 14.

In one embodiment, the light of increasing intensity emanating from the flashlamp 18 is directed to the lasing medium in the dye cell 12 by, for example, a focused reflector 24. The light from the flashlamp 18 is absorbed by the lasing medium and molecules in the lasing medium move from the ground state to excited singlet states. As the excited molecules return to the ground state, photons of a particular wavelength are emitted. Some of the laser light emanates from apertures 26, 28 located at each end of the dye cell 12. A first mirror 32, which is fully reflective, returns emanated laser light back into the dye cell 12. A second mirror 30, which is partially transmissive, returns some of the emanated laser light but allows the pulsed beam 34 to escape.

The ramped input pulse generated by the excitation pulse forming network 14 is a current pulse that is ramp-shaped during substantially the entire duration of the output pulsed beam 34, i.e., the amplitude of the ramped input pulse generally increases with time during substantially the entire duration of the output pulsed beam 34. The amplitude of the ramped input pulse preferably increases by at least about a factor of two during substantially the entire duration of the output pulsed beam 34.

The ramped input (i.e., excitation) pulse generated by the excitation pulse forming network 14 is provided to the flashlamp 18. Because of the shape of the excitation pulse (described in the previous paragraph) provided to the flashlamp 18, the excitation pulse causes the flashlamp 18 to discharge with a similarly-shaped light output intensity (not shown). This discharge excites the lasing medium in the dye cell 12 to "lase" and produce the pulsed beam of laser light 34 of duration greater than 500 microseconds. The ramped excitation pulse counteracts the tendency for the laser 10 to self-terminate (i.e., quench), maintains the laser 10 above the lasing threshold, and consequently causes the laser 10 to generate the output pulsed beam 34 with a duration beyond 500 microseconds.

Figure 2A:
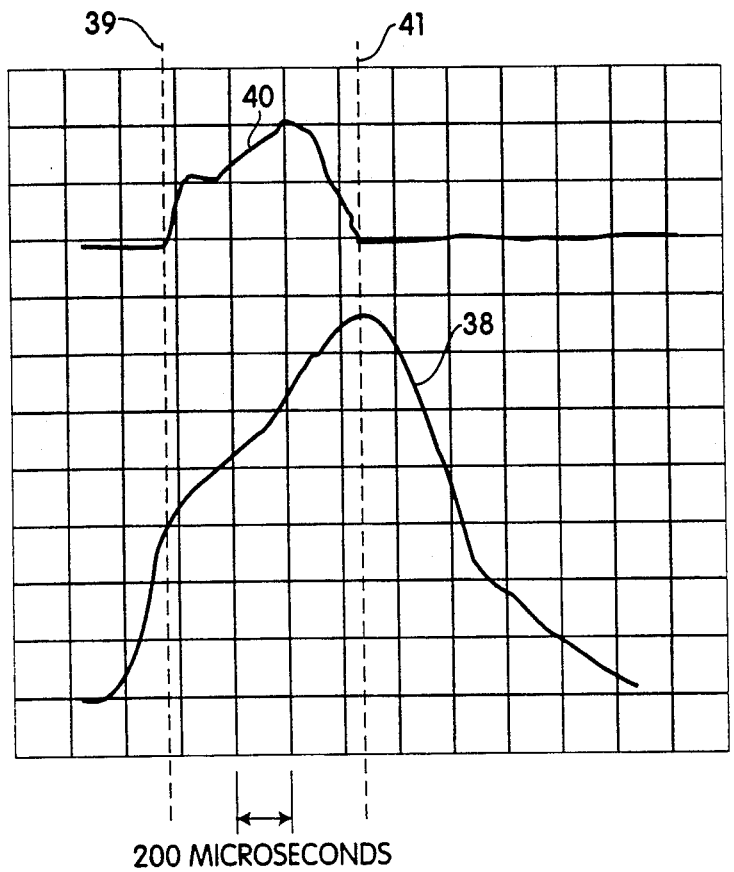

Referring to FIGS. 1 and 2A, in one embodiment, the excitation pulse forming network 14 generates a flashlamp excitation ramped pulse 38 having an amplitude which causes the laser 10 to produce a pulsed beam of laser light 40 with a duration greater than 600 microseconds (about 640 microseconds). In this embodiment, the excitation pulse 38 is a current ramp, and the pulsed beam 40 represents the output intensity of the laser 10. Note that, in accordance with the invention, the amplitude of the excitation pulse 38 generally increases with time during substantially the entire duration of the output pulsed beam 40. From the beginning of the pulsed beam 40 (indicated by a first dotted line 39) to the end of the pulsed beam 40 (indicated by a second dotted line 41), the amplitude of the excitation pulse 38 increases by about a factor of 3.5.

In FIG. 2A, while the vertical axis divisions associated with the excitation pulse 38 can be different from the vertical axis divisions associated with the output pulsed beam 40 (e.g., X amps per division for the pulse 38 and Y Watts per division for the laser beam intensity 40, where X and Y represent real numbers), the vertical axis divisions associated with each signal 38, 40 are linear such that an increase of Z divisions equals a factor of Z increase in amplitude of the signal, where Z represents a real number. The time axis (horizontal axis) divisions in FIG. 2A are each 200 microseconds.

In FIG. 2A, the laser output energy associated with the excitation pulse 38 is approximately 8 Joules, as determined by a laser calorimeter (not shown).

Referring to FIGS. 1 and 2B, in another embodiment, the excitation pulse forming network 14 generates a flashlamp excitation ramped pulse 74 having an amplitude which causes the laser 10 to produce a pulsed beam of laser light 76 with a duration of about 773 microseconds. As in the previous embodiment, the excitation pulse 74 is a current ramp, and the pulsed beam 76 represents the output intensity of the laser 10. Also, in accordance with the invention, the amplitude of the excitation pulse 74 generally increases with time during substantially the entire duration of the output pulsed beam 76.

In FIG. 2B, a first dotted line 75 and a second dotted line 77 indicate a "full-width at half maximum" (FWHM) duration of the pulsed beam 76 of about 773 microseconds. (As known to those of ordinary skill in the art, a FWHM value can be determined by measuring the width of a pulse at half its maximum amplitude.) Note that between the two dotted lines 75, 77, the amplitude of the excitation pulse 74 increases by about a factor of 2. The energy associated with the excitation pulse 74 is approximately 4 Joules, as determined by a laser calorimeter (not shown). The time axis (horizontal axis) divisions in FIG. 2B are each 200 microseconds, and the vertical axis divisions associated with each signal 74, 76 are linear and constant as described previously with reference to FIG. 2A.

Figure 4:
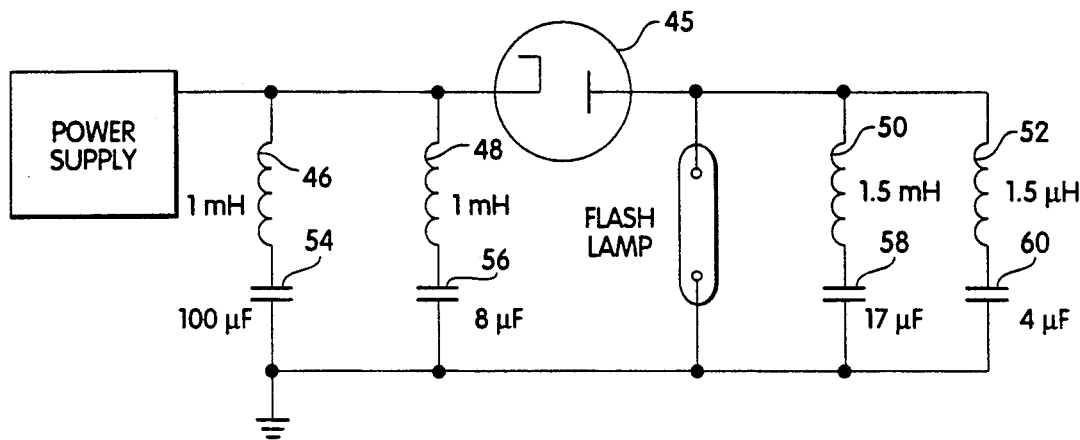
FIG. 4 is a schematic diagram of one embodiment of an electrical circuit according to the invention which is capable of generating a ramped-amplitude excitation pulse for producing a long output pulse from the laser system of FIG. 1.

An excitation pulse forming network according to the invention can be realized in a variety of ways. One example of a circuit capable of providing a flashlamp excitation ramped pulse (such as the pulse 38 of FIG. 2A or the pulse 74 of FIG. 2B) is shown in FIG. 4. The flashlamp excitation ramped pulse produced by this circuit is capable of generating an output pulsed beam of laser light having a duration greater than 500 microseconds, and up to about one millisecond, such as pulsed beam 40 of FIG. 2A or pulsed beam 76 of FIG. 2B. The circuit of FIG. 4 includes an ignitron 45 and energy storage devices such as inductors and capacitors. (Generally, an ignitron is a heavy-duty switch which includes a single-anode pool tube in which an ignitor electrode is employed to initiate a cathode spot on a surface of a mercury pool before each conducting period.) In particular, the circuit has four inductors 46, 48, 50, and 52 with values of 1 mH, 1 mH, 1.5 mH, and 1.5 mH, respectively, and four capacitors 54, 56, 58, and 60 having values of 100 microfarads ($\mu$F), 8 $\mu$F, 17 $\mu$F, and 4 $\mu$F, respectively. A flashlamp and a power supply (e.g., the flashlamp 18 and the power supply 20 of FIG. 1) also are included in the circuit of FIG. 4.

Figure 5:
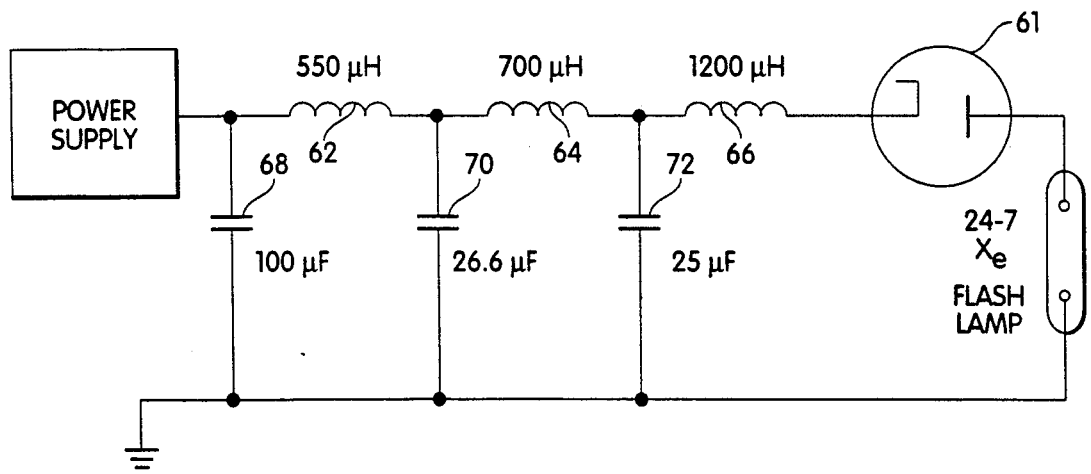
FIG. 5 is a schematic diagram of another embodiment of an electrical circuit according to the invention which is capable of generating a ramped-amplitude excitation pulse for producing a long output pulse from the laser system of FIG. 1.

Another example of a circuit capable of providing a flashlamp excitation ramped pulse according to the invention is shown in FIG. 5. This circuit includes an ignitron 61, three inductors 62, 64, and 66 with values of 550 microhenries ($\mu H$), 700 $\mu H$, and 1200 $\mu H$, respectively, and three capacitors 68, 70, and 72 having values of 100 $\mu F$, 26.6 $\mu F$, and 25 $\mu F$, respectively. A flashlamp and a power supply (e.g., the flashlamp 18 and the power supply 20 of FIG. 1) also are included in the circuit of FIG. 5.

The flashlamp shown in FIGS. 4 and 5 (and the flashlamp 18 of FIG. 1) can be, for example, a xenon light source.

Both the circuit of FIG. 4 and the circuit of FIG. 5 are capable of generating flashlamp excitation ramped pulses which result in a laser according to the invention producing output pulsed beams of laser light having durations greater than 500 microseconds and up to approximately one millisecond.

Other modifications and implementations will occur to those skilled in the art without departing from the spirit and the scope of the invention as claimed. Accordingly, the invention is to be defined not by the preceding illustrative description, but by the following claims.

What is claimed is:

1. A method of generating a pulsed beam of laser light of long duration from a flashlamp-excited laser, comprising:
   generating a ramp pulse having an amplitude which generally increases with time during substantially the entire duration of a pulsed beam of laser light produced by a flashlamp-excited laser, and
   driving the flashlamp-excited laser with the ramp pulse.

2. The method of claim 1 wherein the duration of the pulsed beam of laser light is greater than 500 microseconds.

3. The method of claim 1 wherein the amplitude of the ramp pulse increases by a factor of about 2 or greater during substantially the entire duration of the pulsed beam of laser light.

4. The method of claim 1 wherein the pulsed beam of laser light has an energy level of about 0.5 Joules or greater.

5. The method of claim 1 wherein the flashlamp-excited laser is used to treat cutaneous vascular lesions.

6. The method of claim 1 wherein a lasing medium associated with the flashlamp-excited laser comprises a dye carried by a liquid.

7. A method of generating a pulsed beam of laser light of long duration, comprising:
   providing a flashlamp-excited dye laser for producing a pulsed beam of laser light,
   generating a ramp pulse having an amplitude which generally increases with time during substantially the entire duration of the pulsed beam of laser light, and
   driving the flashlamp-excited laser with the ramp pulse.

8. A flashlamp-excited laser for producing a pulsed beam of laser light of long duration, comprising:
   a flashlamp driven by a pulse forming circuit which generates a ramp pulse having an amplitude generally increasing with time during substantially the entire duration of a pulsed beam of laser light produced by the laser.

9. The flashlamp-excited laser of claim 8 wherein a lasing medium associated with the laser comprises a dye carried by a liquid.

10. The flashlamp-excited dye laser of claim 9 wherein the duration of the pulsed beam of laser light is greater than 500 microseconds.

11. The flashlamp-excited dye laser of claim 10 wherein the amplitude of the ramp pulse increases by a factor of about 2 or greater during substantially the entire duration of the pulsed beam of laser light.

12. The flashlamp-excited dye laser of claim 11 wherein the pulsed beam of laser light has an energy level of about 0.5 Joules or greater.

13. The flashlamp-excited dye laser of claim 12 wherein the laser is used to treat cutaneous vascular lesions.

* * * * *